US012618831B2

(12) United States Patent
An et al.

(10) Patent No.: US 12,618,831 B2
(45) Date of Patent: May 5, 2026

(54) IMMUNE REACTION ANALYSIS DEVICE EQUIPPED WITH INCUBATION CHAMBER

(71) Applicant: BODITECH MED INC., Gangwon-Do (KR)

(72) Inventors: Jae Un An, Incheon (KR); Dong Ki Park, Seoul (KR); Uk Bin Im, Gangwon-Do (KR); Youn Tae Im, Gangwon-do (KR); Min Seok Cha, Gangwon-do (KR); Kang Hyuk Lee, Gangwon-do (KR); Jae Ho Park, Seoul (KR); Jeong Ae Shin, Gangwon-do (KR)

(73) Assignee: BODITECH MED INC., Chuncheon-si (KR)

( * ) Notice: Subject to any disclaimer, the term of this patent is extended or adjusted under 35 U.S.C. 154(b) by 538 days.

(21) Appl. No.: 18/258,659

(22) PCT Filed: Dec. 3, 2021

(86) PCT No.: PCT/KR2021/018262
§ 371 (c)(1),
(2) Date: Jun. 21, 2023

(87) PCT Pub. No.: WO2022/154261
PCT Pub. Date: Jul. 21, 2022

(65) Prior Publication Data
US 2024/0044875 A1    Feb. 8, 2024

(30) Foreign Application Priority Data
Jan. 18, 2021    (KR) ........................ 10-2021-0006961

(51) Int. Cl.
*G01N 33/53* (2006.01)
*B01L 3/00* (2006.01)

(52) U.S. Cl.
CPC .... *G01N 33/5302* (2013.01); *B01L 3/502715* (2013.01); *B01L 2200/025* (2013.01);
(Continued)

(58) Field of Classification Search
CPC ........... B01L 2200/025; B01L 2200/04; B01L 2200/16; B01L 2300/021;
(Continued)

(56) References Cited

U.S. PATENT DOCUMENTS 6,228,636 B1 * 5/2001 Yahiro ................. G01N 35/028
435/303.1
10,670,499 B2    6/2020 Kim et al.

FOREIGN PATENT DOCUMENTS

EP            3916077 A1 * 12/2021    ....... G01N 35/00732
JP       10-062433 A     3/1998
(Continued)

OTHER PUBLICATIONS

International Search Report and Written Opinion received for PCT Application Serial No. PCT/KR2021/018262 dated Mar. 16, 22, 21 pages.
(Continued)

*Primary Examiner* — Jennifer Wecker
(74) *Attorney, Agent, or Firm* — Klintworth & Rozenblat LLP

(57) ABSTRACT

The present invention relates to an immune reaction analysis device. The analysis device of the present invention comprises: an incubation chamber which has a plurality of slits for accommodating cartridges, and in which an incubation for an immunodiagnostic reaction is performed; a cartridge input driving unit for inputting the cartridge into the slit of the incubation chamber; a determination unit for determining the result of the reaction in the cartridge; a cartridge withdrawal driving unit for withdrawing the cartridge
(Continued)

accommodated in the slit of the incubation chamber; a cartridge transfer driving unit for transferring the withdrawn cartridge to the determination unit; and a control unit for controlling the cartridge input driving unit, the cartridge withdrawal driving unit, and the cartridge transfer driving unit. The immune reaction analysis device of the present invention provides excellent ease of use and can accurately perform a good number of incubations.

12 Claims, 15 Drawing Sheets

(52) U.S. Cl.
CPC ....... *B01L 2200/04* (2013.01); *B01L 2200/16* (2013.01); *B01L 2300/021* (2013.01); *B01L 2300/0663* (2013.01); *B01L 2300/1822* (2013.01)

(58) Field of Classification Search
CPC ..... B01L 2300/0663; B01L 2300/1822; B01L 3/502715; G01N 2035/00356; G01N 2035/00752; G01N 33/5302; G01N 35/00
See application file for complete search history.

(56) References Cited

FOREIGN PATENT DOCUMENTS

| | | |
|---|---|---|
| KR | 10-2054862 B1 | 12/2019 |
| KR | 10-2020-0055913 A | 5/2020 |
| WO | 2020/124255 A1 | 6/2020 |

OTHER PUBLICATIONS

International Preliminary Report on Patentability received for PCT Application Serial No. PCT/KR2021/018262 dated Jul. 27, 2023, 9 pages.

* cited by examiner 2020.08.28 / 00:05:43 pm     25.0℃ 🖨 ◁ (A)

| Analyses | History | QC | Settings |
|---|---|---|---|

| ◯ | Date&Time | name | Item | Result(16) |
|---|---|---|---|---|
| ◯ | 02.01.2020 01:49:22 am | L2 | COVID-19 Ab | IgM 0.0:N IgG 0.0:N |
| ◯ | 02.01.2020 01:46:44 am | L8 | iFOB | Negative < 25.00 |
| ◯ | 02.01.2020 01:40:12 am | L8 | Tn-I | 15.66 ng/mL 15.66 ug/L |
| ◯ | 02.01.2020 01:41:27 am | H2 | iFOB | Positive > 1000.00 |
| ◯ | 02.01.2020 01:40:53 am | H8 | iFOB | Positive > 1000.00 |
| ◯ | 02.01.2020 01:37:22 am | H3 | Tn-I | 6.37 ng/mL 6.37 ug/L |
| ◯ | 02.01.2020 01:36:56 am | L2 | Tn-I | 8.22 ng/mL 8.22 ug/L |
| ◯ | 02.01.2020 01:35:26 am | Z | PCT plus | 0.56 ng/mL |
| ◯ | 02.01.2020 01:35:00 am | H3 | PCT plus | 0.88 ng/mL |
| ◯ | 02.01.2020 01:34:21 am | H2 | PCT plus | 0.54 ng/mL |
| ◯ | 02.01.2020 01:33:14 am | L6 | PCT plus | < 0.02 ng/mL |

| Search | Print | LIS |
|---|---|---|
| Delete | Prev page | Next page |

FIG. 19

IMMUNE REACTION ANALYSIS DEVICE EQUIPPED WITH INCUBATION CHAMBER

TECHNICAL FIELD

The present invention relates to an immune reaction analysis device, and more particularly to an immune reaction analysis device equipped with an incubation chamber.

BACKGROUND ART

With the development of technology in various related fields such as medicine and biotechnology, the tests for detecting various molecular indicators such as blood cells, genes, proteins, antigens, and pathogens in predetermined biological samples such as urine and blood have been widely performed. The inspection process is generally performed by taking a sample, reacting the collected sample with a predetermined reagent suitable for a desired indicator, and then analyzing and observing changes that occur. in this way, it is possible to perform qualitative and/or quantitative analysis on various molecular indicators included in the sample, and based on this, information on diagnosis, progression, prognosis, etc. of the disease can be obtained.

The immune reaction based on specific binding between antigens/antibodies is widely used for such testing. Immune reaction technologies include a chromogenic method, a chemiluminescent method, a method using fluorescence, and the like, depending on the type of substrate used for the detection of an analyte.

The immune reaction requires incubation for the reaction of reagents and samples. When using an analysis device without an incubation chamber, the user must perform incubation in a separate device. In this case, if a large number of tests are performed, it is so hard to control the incubation time for individual cartridges, that it is difficult to make an accurate diagnosis. In addition, since the user has to carry the incubated cartridge to the reading device, the user's workload increases.

DETAILED DESCRIPTION OF THE INVENTION

Technical Problem

Accordingly, an objective of the present invention is to provide an immune reaction analysis device with excellent usability.

In addition, another objective of the present invention is to provide an immune reaction analysis device that performs a large number of incubations more accurately.

In addition, another objective of the present invention is to provide an immune reaction analysis device with improved cartridge throughput per unit time.

Technical Solution

The present invention for achieving the above-mentioned objectives provides an immune reaction analysis device comprising: an incubation chamber which has a plurality of slits for accommodating cartridges, and in which an incubation for an immunodiagnostic reaction is performed; a cartridge input driving unit for inputting the cartridge into the slit of the incubation chamber; a determination unit for determining the result of the reaction in the cartridge; a cartridge withdrawal driving unit for withdrawing the cartridge accommodated in the slit of the incubation chamber;

a cartridge transfer driving unit for transferring the withdrawn cartridge to the determination unit; and a control unit for controlling the cartridge input driving unit, the cartridge withdrawal driving unit, and the cartridge transfer driving unit.

Preferably, the immune reaction analysis device further comprises a cartridge discharge driving unit for discharging a corresponding cartridge to the outside after an immune reaction result in the cartridge located in the determination unit is completely determined. The cartridge discharge driving unit includes a sensor for detecting whether or not the cartridge is discharged.

Preferably, a plurality of slots are disposed in the incubation chamber in a direction perpendicular to the driving direction of the cartridge input driving unit. The incubation chamber includes: a shelf having a plurality of the slits formed thereon; and a shelf elevation unit for driving the shelf in a vertical direction. The incubation chamber further includes a Peltier element attached to the shelf. The incubation chamber further includes a temperature sensor attached to the shelf. The control unit controls the Peltier element according to the measured value of the temperature sensor.

Preferably, the incubation chamber further includes a chamber case for accommodating the shelf and the shelf elevation unit. On the front surface of the chamber case, a chamber inlet for inputting a cartridge is formed at a first height and a chamber through-hole is formed at a second height. The cartridge input driving unit includes an injector for inputting a cartridge into a slit positioned at the first height of the incubation chamber through the chamber inlet. A chamber outlet is formed at the second height on the rear surface of the chamber case. The cartridge transfer driving unit includes an ejector for transferring the cartridge accommodated in the slit located at the second height of the incubation chamber to the determination unit through the chamber outlet. The control unit drives the shelf elevation unit to position the slit from the first height to the second height after a preset incubation time elapses.

Preferably, the incubation chamber further includes: a cartridge sensor installed at an inlet of the slit; and a cartridge sensor installed at an outlet of the slit. The control unit drives the shelf elevating unit after determining whether the cartridge is completely input or discharged by means of the cartridge sensor.

Preferably, the immune reaction analysis device according to the present invention further comprises: a camera module for photographing a housing of the cartridge which is input into a slit of the incubation chamber by means of the cartridge input driving unit; and a user interface for displaying a specific location of the cartridge housing photographed by the camera module. The immune reaction analysis device according to the present invention further comprises: a barcode recognition module for recognizing a barcode printed on the housing of the cartridge which is input into the slit of the incubation chamber by means of the cartridge input driving unit.

Technical Effects

As described above, the analysis device of the present invention has excellent usability. In addition, even a large number of incubations can be performed more accurately. Also, the cartridge throughput per unit time is increased.

BRIEF DESCRIPTION OF THE DRAWINGS

FIG. 19 illustrates a screen displayed on the user interface shown in FIG. 1A.

BEST MODE FOR ACCOMPLISHING THE INVENTION

Figure 1A:
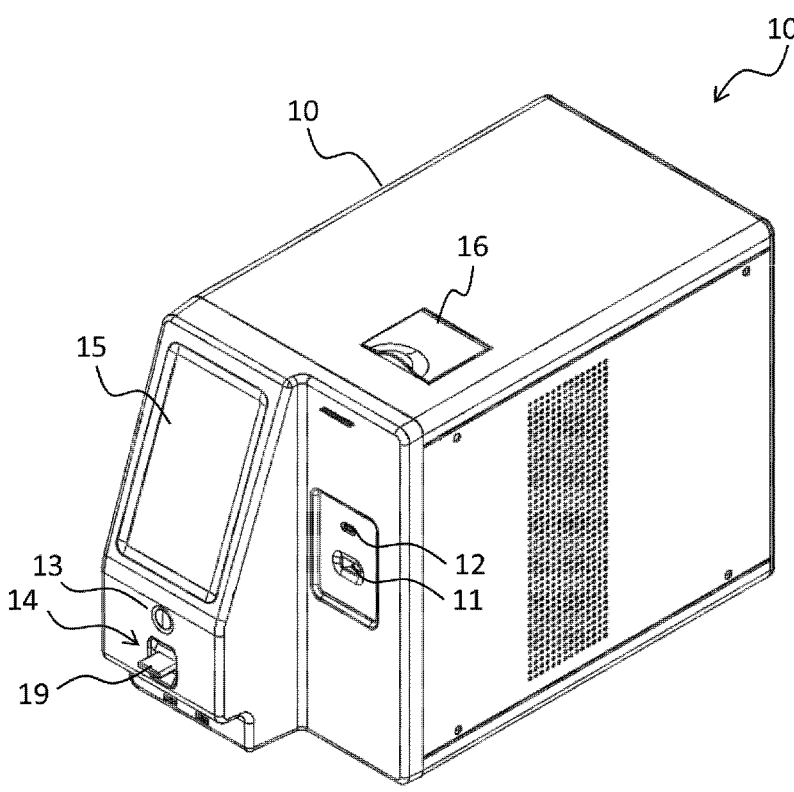
FIG. 1A shows a front exterior of the immune reaction analysis device according to an embodiment of the present invention.

Hereinafter, embodiments of the present invention will be described in detail with reference to the accompanying drawings. Terms used in this description should not be construed as being limited to conventional or dictionary meanings. Therefore, the embodiments described in this specification and the configurations shown in the drawings are only one of the most preferred embodiments of the present invention and do not represent all of the technical ideas of the present invention, so that it should be understood that there may be various equivalents and modifications that can replace them at the time of this application. In the entire drawing, those having the same function are given the same reference numerals, and detailed description thereof will be omitted.

Figure 1B:
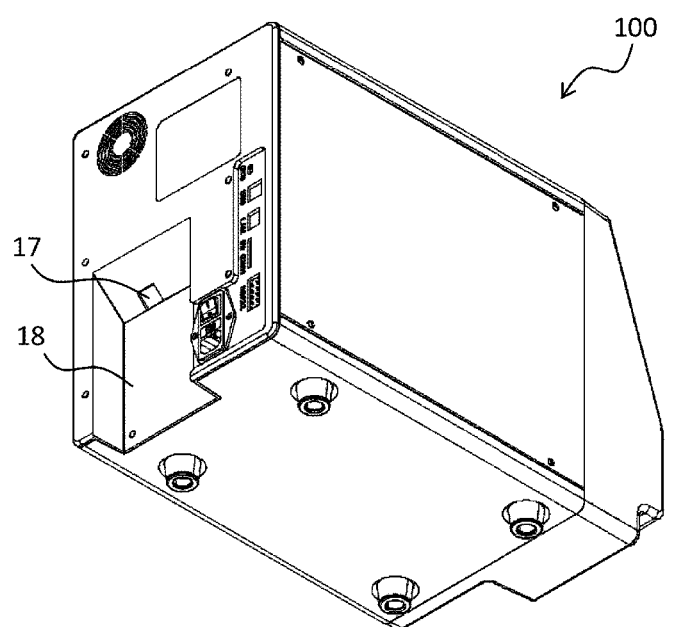
FIG. 1B shows the back exterior thereof.

FIG. 1A shows a front exterior of the immune reaction analysis device 100 according to an embodiment of the present invention, and FIG. 1B shows the back exterior thereof. As shown in drawings, the immune reaction analysis device 100 has a housing 10. The housing 10 includes a cartridge inlet 11, a cover status light 12, a power button 13, an ID chip inlet 14, a user interface 15, a built-in printer 16, a cartridge outlet 17, a cartridge waste box mounting portion 18 and the like.

A cartridge is mounted into the cartridge holder (502 in FIG. 5) through the cartridge inlet 11. A hold cover (not shown) is installed at the cartridge inlet 11 in order to prevent foreign substances such as light and dust from entering the immune reaction analysis device 100. The cover status light 12 indicates whether or not the cartridge can be input into the immune reaction analysis 100 to perform analysis. An ID chip 19 storing cartridge information is inserted into the ID chip inlet 14. The ID chip is inserted into the ID chip inlet 14 and the information on the ID chip is read and stored in the internal memory (not shown) of the immune reaction analysis device 100, and is used even for the next cartridge until a new ID chip 19 is inserted. The user interface 15 may be implemented with an LCD, and as a display, not only displays various states of the immune reaction analysis device 100, test results, etc., but is also used as a touchpad to input various information necessary for diagnosis. Diagnosis results are printed by the built-in printer 16.

The cartridge used in the immune reaction analysis device 100 is discharged through the cartridge outlet 17. As a cartridge waste box (not shown) is mounted on the cartridge waste box mounting portion 18, cartridges discharged through the cartridge outlet 17 can be collected without user intervention.

Figure 2:
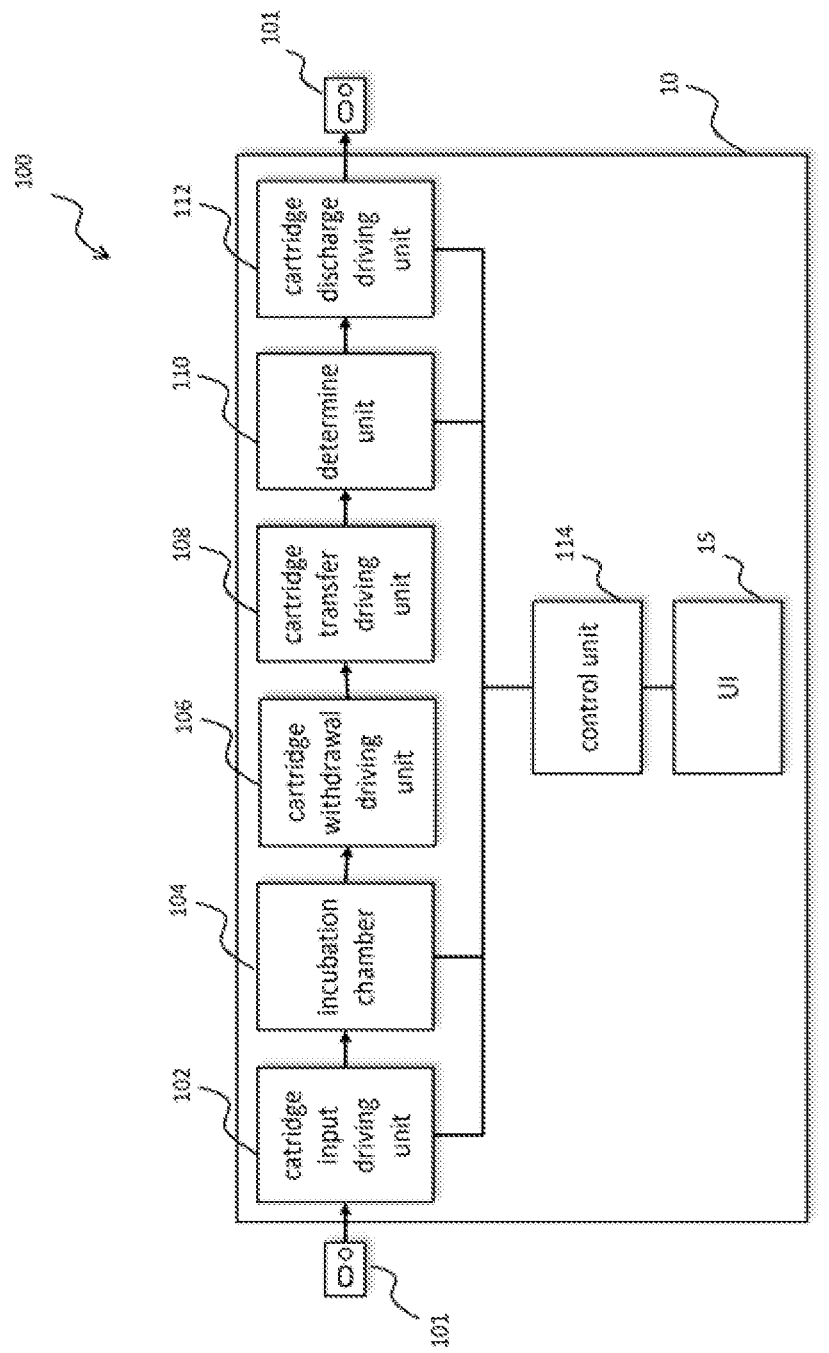
FIG. 2 illustrates the main functions of the immune reaction analysis device shown in FIG. 1A.
Figure 3:
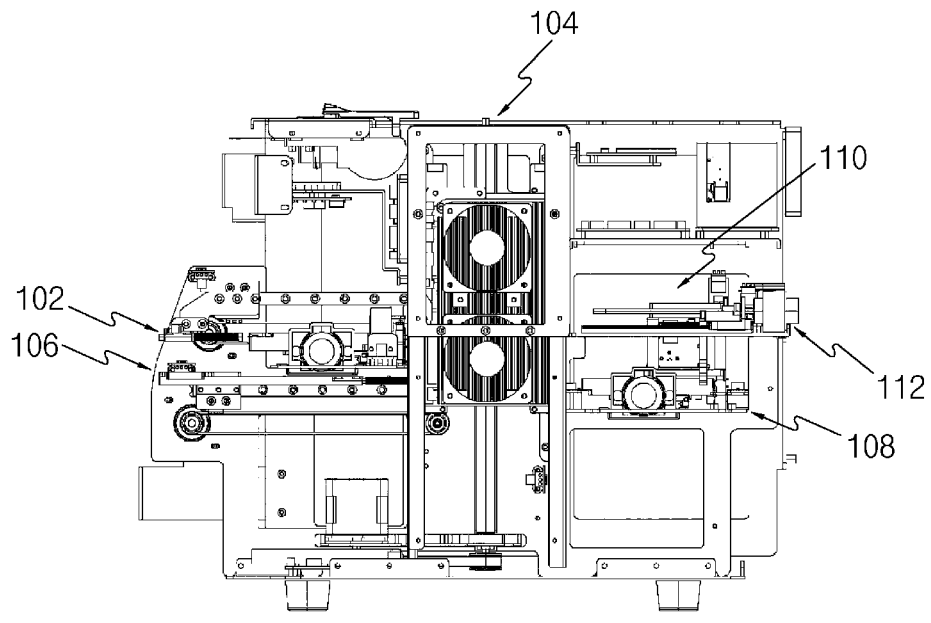
FIG. 3 is a side view of the immune reaction analysis device shown in FIG. 1A without its housing.

FIG. 2 illustrates the main functions of the immune reaction analysis device 100, and FIG. 3 is a side view of the immune reaction analysis device 100 without its housing. As shown in drawings, the immune reaction analysis device 100 includes a cartridge input driving unit 102, an incubation chamber 104, a cartridge withdrawal driving unit 106, a cartridge transfer driving unit 108, a determination unit 110, a cartridge discharge driving unit 112, a control unit 114, and the like.

When the user inputs the cartridge 101 through the cartridge inlet 11 and hits the diagnosis start button by use of the user interface 15, the cartridge input driving unit 102 inserts the cartridge 101 into the slit of the incubation chamber 104. The incubation chamber 104 has a plurality of slits accommodating the cartridge 101. Incubation (or culture) for a diagnostic reaction is performed in the cartridge 101 while being accommodated in the slit of the incubation chamber 104. The cartridge withdrawal driving unit 106 withdraws the cartridge 101 from the slit of the incubation chamber 104 when culturing is completed. The cartridge transfer driving unit 108 transfers the cartridge withdrawn from the incubation chamber 104 to the determination unit 110. The determination unit 110 determines the reaction result in the cartridge 101. The cartridge discharge driving unit 112 discharges the cartridge 101 for which determination has been completed, from the determination unit 110 to the outside of the immune reaction analysis device 100. The control unit 114 controls all operations of the immune reaction analysis device 100.

Figure 4:
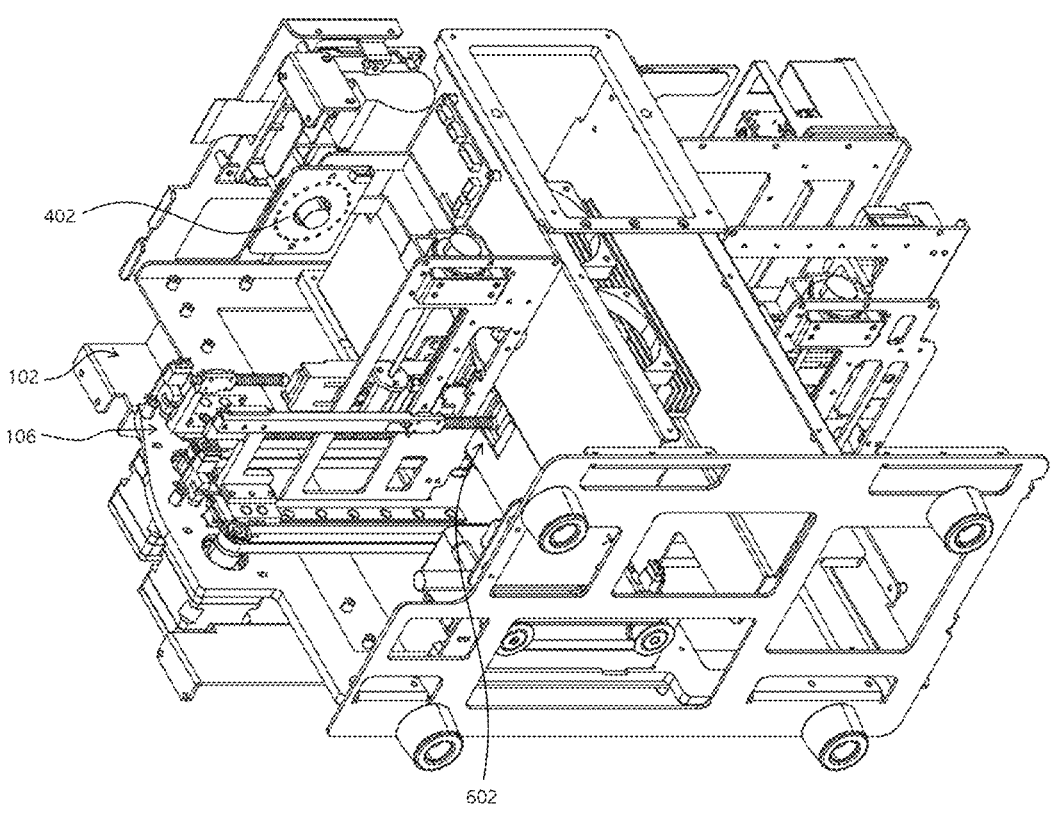
FIG. 4 illustrates the configuration of a cartridge input driving unit and a cartridge withdrawal driving unit of the immune reaction analysis device shown in FIG. 3.
Figure 5:
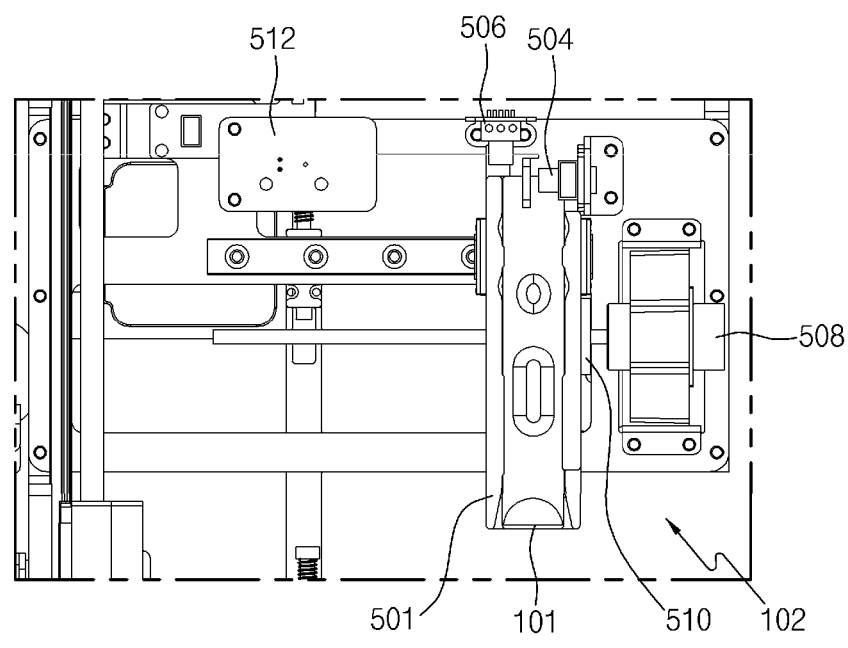
FIG. 5 illustrates the cartridge mounting in the cartridge input driving unit shown in FIG. 3.
Figure 6:
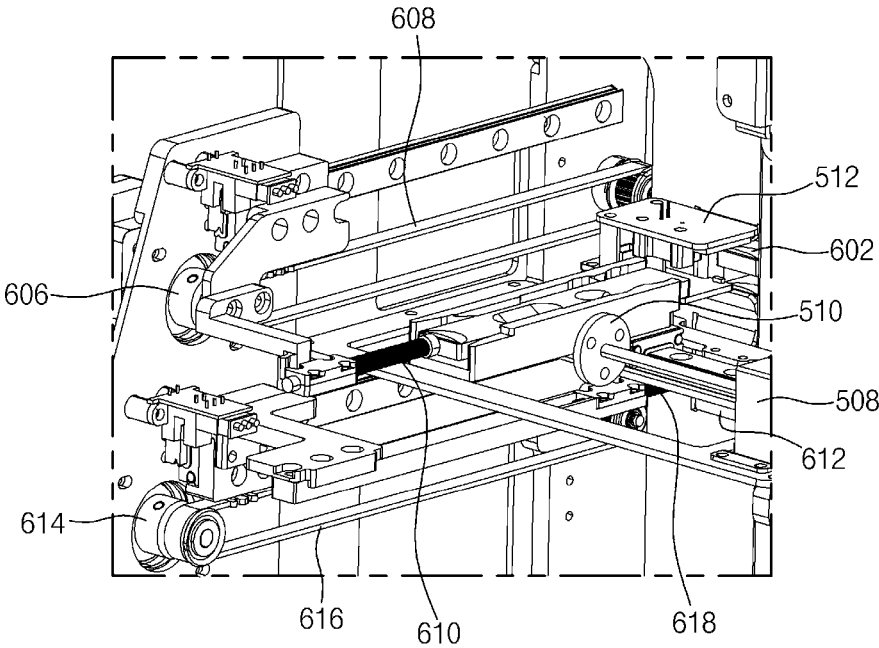
FIG. 6 illustrates cartridge transfer in the cartridge input driving unit shown in FIG. 3.
Figure 7:
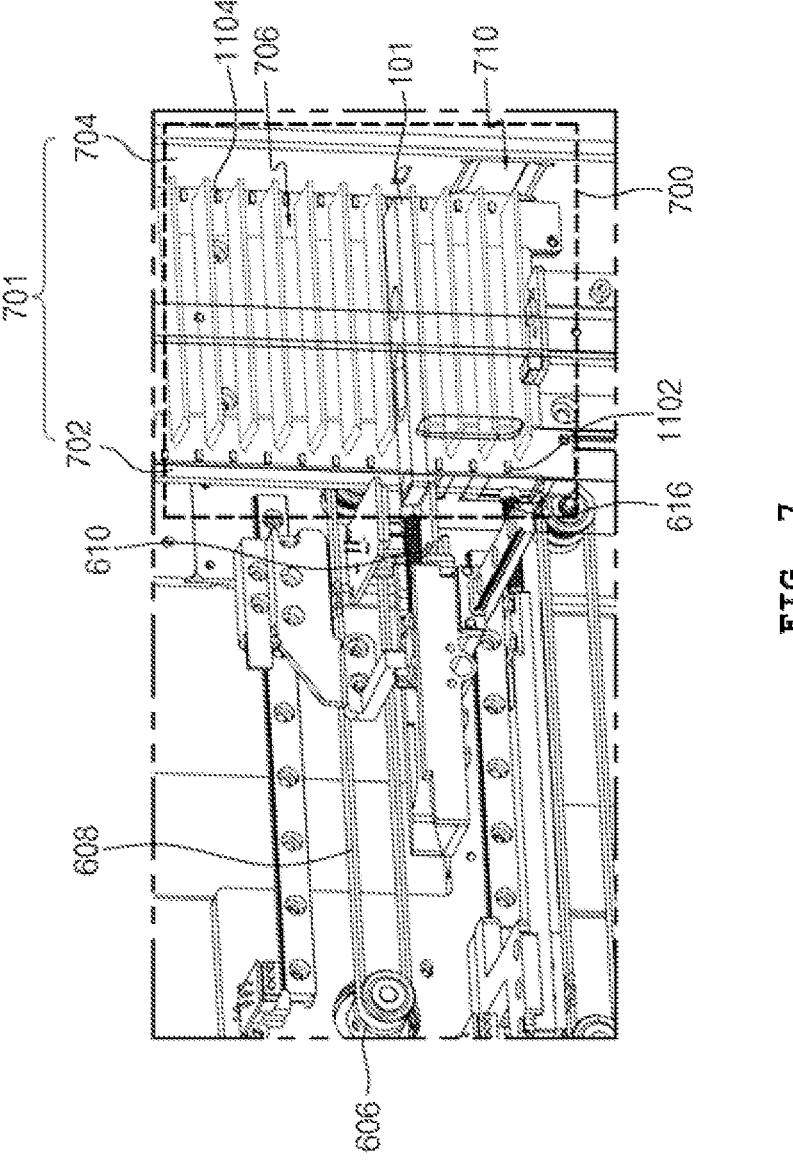
FIG. 7 illustrates a state in which a cartridge is input into an incubation chamber by the cartridge input driving unit shown in FIG. 3.

FIG. 4 illustrates the configuration of a cartridge input driving unit 102 and a cartridge withdrawal driving unit 106 of the immune reaction analysis device 100. FIG. 5 illustrates the cartridge mounting in the cartridge input driving unit 102. FIG. 6 illustrates cartridge transfer in the cartridge input driving unit 102. FIG. 7 illustrates a state in which a cartridge is input into an incubation chamber by the cartridge input driving unit 102.

As shown in FIGS. 4 to 6, the cartridge input driving unit 102 includes a cartridge holder 502, a cartridge recognition sensor 504, an initial position recognition sensor 506, a motor 508, a moving block 510, a camera module (402 shown in FIG. 4), a barcode recognition module 512, a motor 606, a belt 608, an injector 610, and the like.

The cartridge holder 502 is detected by the initial position recognition sensor 506, and then is moved to the cartridge inlet 11 spaced a certain distance apart. When the cartridge 101 is mounted into the cartridge holder 502 through the cartridge inlet 11, the control unit 114 checks whether the cartridge 101 is present by means of the cartridge recognition sensor 504.

As shown in FIG. 6, the control unit 114 drives the moving block 510 by the motor 508 to transfer the cartridge 101 mounted in the cartridge holder 502 so that the cartridge 101 may be photographed by the camera module 402. The camera module 402 photographs the cartridge 101, and the control unit 114 makes the subject identification marks recorded at a specific location of the housing of the cartridge 101 be displayed on the user interface 15. In this way, a user can easily identify a cartridge without inputting identification information on a specific cartridge by use of the user interface 15.

After the camera module 402 completes photographing the cartridge 101, the control unit 114 transfers the cartridge holder 502 to the chamber inlet 602 by means of the motor 508 and the moving block 510. Next, the control unit 114 drives the injector 610 by the motor 606 and the belt 608 so to push the cartridge 101 into the chamber inlet 602. An elastic body such as a spring is installed at the front end of the injector 610 so to prevent the cartridge 101 from being excessively pushed into the incubation chamber 104. While pushing the cartridge 101 into the incubation chamber 104 by use of the injector 610, the barcode recognition module 604 reads the barcode printed on the housing of the cartridge 101.

A part 700 indicated by a dotted line in FIG. 7 is a cross-sectional view of the incubation chamber 104. As shown in FIG. 7, the incubation chamber 104 includes a chamber case 701, and the chamber case 701 includes a front panel 702 and a rear panel 704. The front panel 702 is formed with a chamber inlet 602 for inputting a cartridge and a chamber through-hole 612 for withdrawing a cartridge. The rear panel 704 is formed with a chamber outlet 710 through which the cartridge stored in the slit 706 of the incubation chamber 104 is withdrawn. A position corresponding to the height of the chamber inlet 602 on the rear panel 704 is blocked to prevent the cartridge from escaping. The chamber through-hole 612 and the chamber outlet 710 are formed at the same height.

Figure 8:
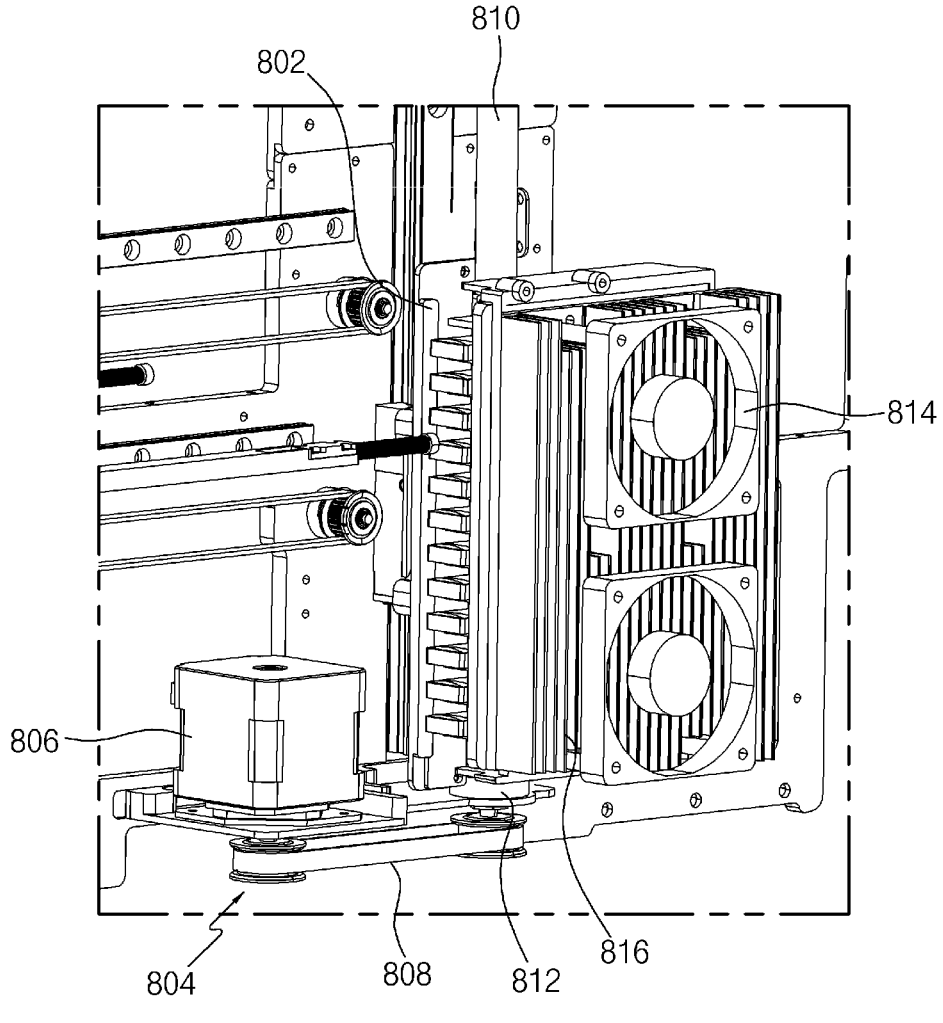
FIG. 8 illustrates a state in which the front panel of the incubation chamber shown in FIG. 3 is removed.
Figure 9A:
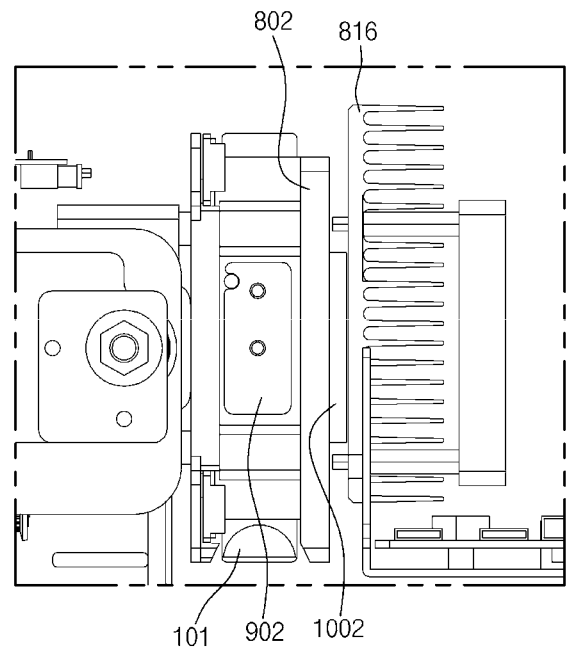
FIGS. 9A and 9B illustrates a temperature sensor installed in the incubation chamber shown in FIG. 8.
Figure 9B:
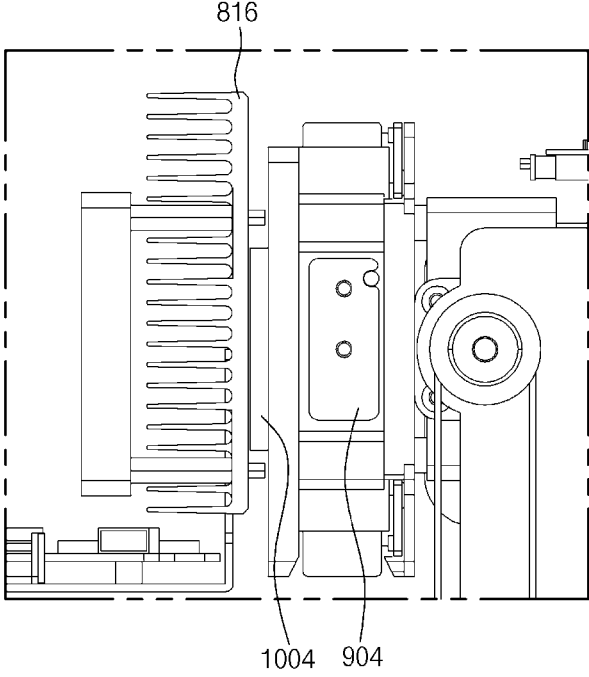
Figure 10:
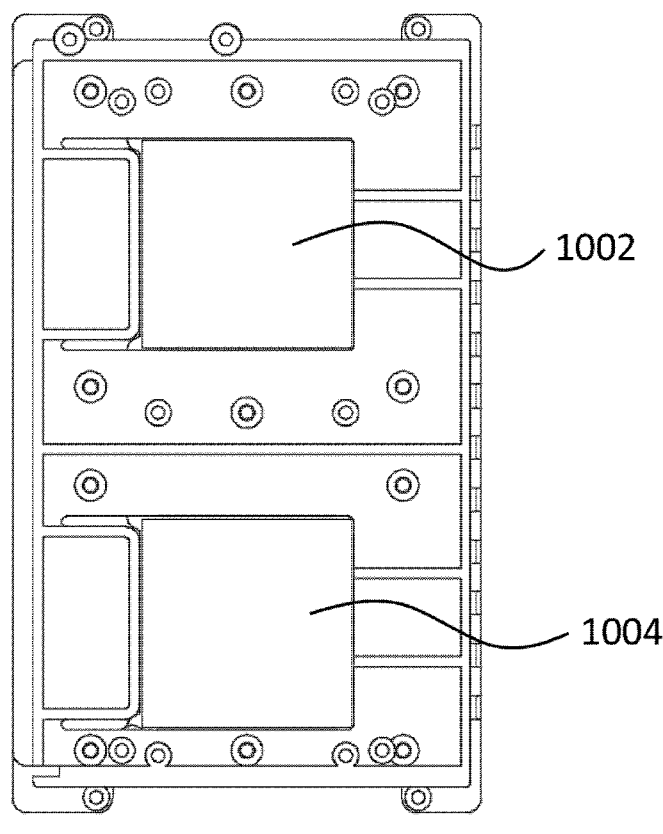
FIG. 10 illustrates a Peltier element installed in the incubation chamber shown in FIG. 8.

FIG. 8 illustrates a state in which the front panel of the incubation chamber 104 is removed, and FIGS. 9A and 9B illustrates a temperature sensor installed in the incubation chamber 104. FIG. 10 illustrates a Peltier element installed in the incubation chamber 104.

As shown in FIG. 8, the incubation chamber 104 includes a shelf 802 and a shelf elevation unit 804 inside a chamber case 701. The shelf 802 is formed with a plurality of slits 706 in a direction perpendicular to the driving direction of the injector 610. The shelf elevation unit 804 drives the shelf 802 in the vertical direction. By arranging the slots 706 in the vertical direction, the volume of the immune reaction analysis device 100 can be reduced, and the simple driving mechanism can be configured.

The shelf elevation unit 804 includes a motor 806, a belt 808, a shaft 810, a moving block 812, and the like. The moving block 812 converts the rotational motion transmitted from the motor 806 by the belt 808 into an ascending and descending motion in the direction of the shaft 810. In order to input the cartridge 101 into the incubation chamber 104, the control unit 114 drives the shelf elevation unit 804 so that the empty slot may be located at the height of the chamber inlet 602. In addition, when incubation in the cartridge stored in a specific slit of the incubation chamber 104 is completed, the control unit 114 drives the shelf elevation unit 804 so to locate the corresponding slot at the height of the chamber outlet 710.

The incubation chamber 104 includes a fan 814, a heat sink 816, temperature sensors 902 and 904, Peltier elements 1002 and 1004, and the like, so that the shelf 802 may maintain a specific temperature for incubation.

The temperature sensor 902 is attached to the upper surface of the shelf 802 as shown in FIG. 9A, while the temperature sensor 904 is attached to the lower surface of the shelf 802 as shown in FIG. 9B. By attaching temperature sensors to the upper and lower surfaces of the shelf 802, the temperature of the entire shelf 802 can be reliably measured. The Peltier elements 1002 and 1004 are installed between the shelf 802 and the heat sink 816 as shown in FIGS. 9A, 9B, and 10.

The control unit 114 operates the Peltier elements 1002 and 1004 according to the temperature of the shelf 802 measured by the temperature sensors 902 and 904. The fan 814 and the heat sink 816 release heat from the incubation chamber 104 to the outside. The incubation chamber 104 in this embodiment maintains a specific temperature in the range between 22 and 35 degrees depending on the type of diagnosis, and has 12 slots.

As shown in FIG. 7, the incubation chamber 104 has cartridge sensors 1102 at the entrance and cartridge sensors 1104 at the exit in every slot. The control unit 114 determines whether a cartridge is present in a given slot and whether the cartridge is stuck during its being transferred to the slot, using the detection signals from the cartridge sensors 1102 and 1104. The cartridge sensors 1102 and 1104 may use light or ultrasonic waves to scan the cartridge 101 accommodated in the slot 706 to measure reflected signals.

The incubation time starts from the time when the user inputs the cartridge 101 and selects the diagnosis start button on the user interface 15. When the preset incubation time elapses, the control unit 114 drives the shelf elevation unit 804 to locate the corresponding slit at the height of the chamber outlet 710, and controls the cartridge withdrawal driving unit 106 to withdraw the cartridge 101 from the slit. In this way, the incubation time is independently controlled for each slot.

The control unit 114 checks whether or not there is any cartridge that has not been input or withdrawn by means of the cartridge sensors 1102 and 1104 before driving the shelf elevation unit 804. If the shelf elevation unit 804 is driven when a cartridge 101 has not been input or withdrawn, the cartridge 101 may be damaged. If there is any cartridge that has not yet been input into the incubation chamber 104 completely, the control unit 114 drives the shelf elevation unit 804 only after completing the cartridge input by the cartridge input driving unit 102. If there is any cartridge that has not been withdrawn from the incubation chamber 104, the control unit 114 drives the shelf elevation unit 804 only after completing the cartridge withdrawal by the cartridge withdrawal driving unit 106.

Figure 11:
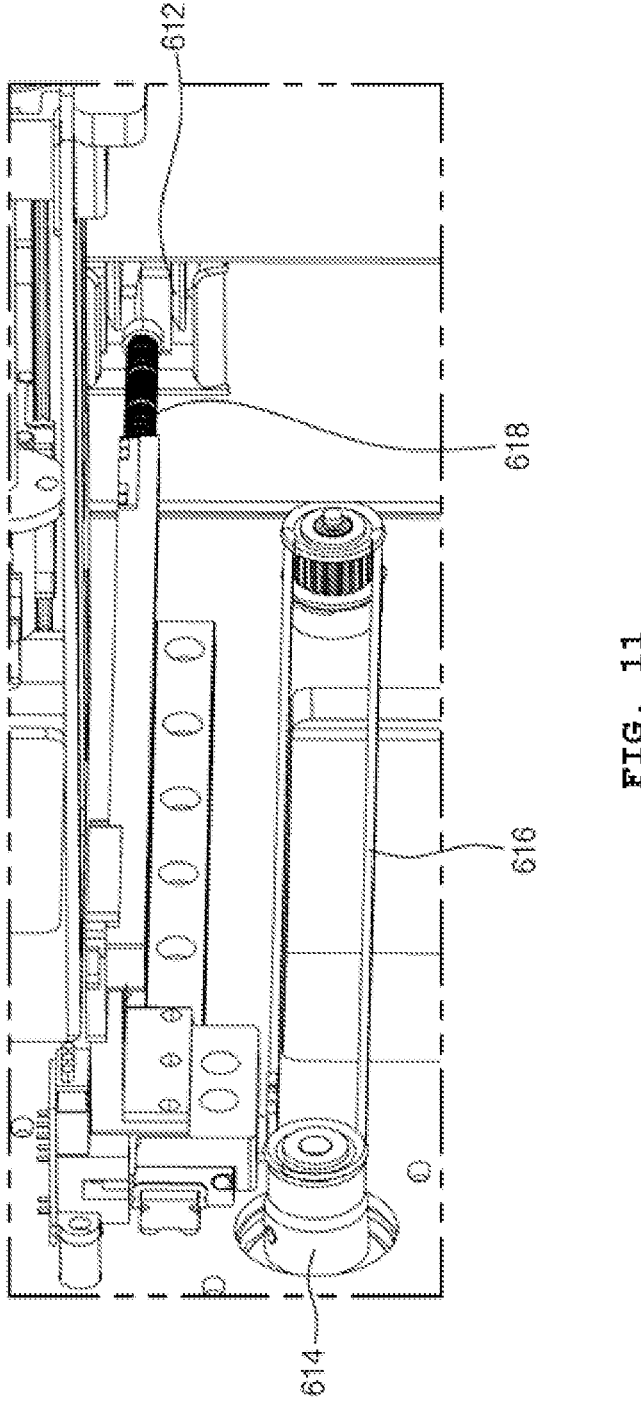
FIG. 11 illustrates the cartridge withdrawal driving unit shown in FIG. 3.
Figure 12:
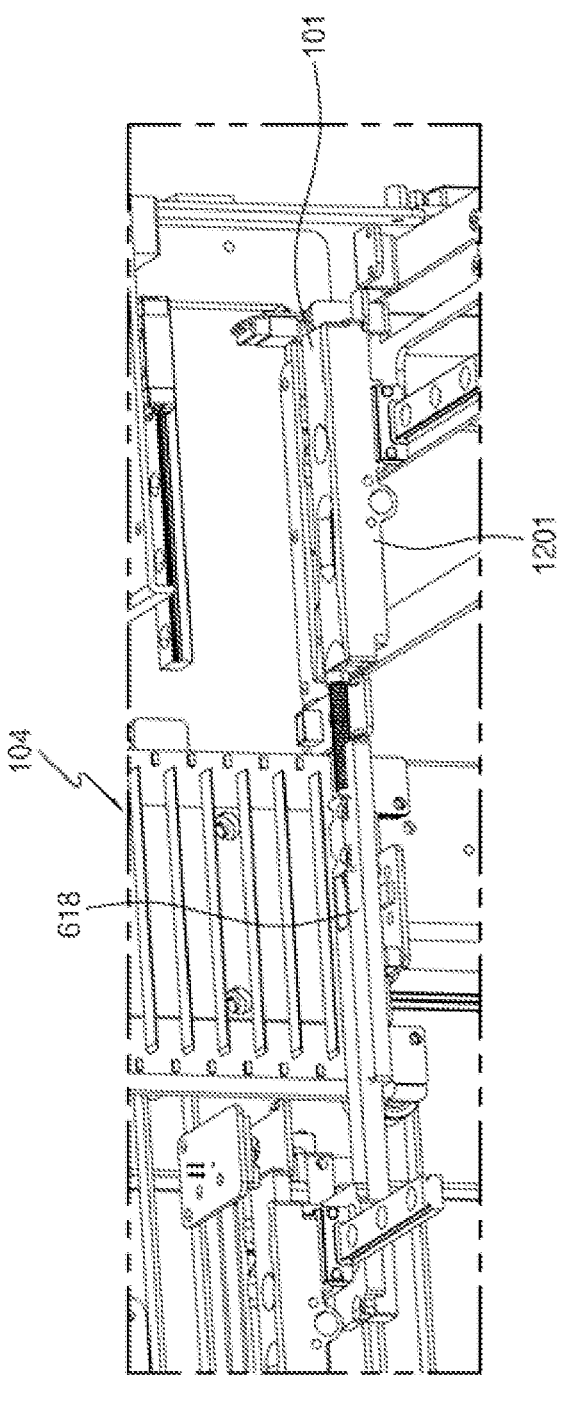
FIG. 12 illustrates a state in which a cartridge is withdrawn from a slot of an incubation chamber by the cartridge withdrawal driving unit shown in FIG. 11.

FIG. 11 illustrates the cartridge withdrawal driving unit 106 shown in FIG. 3, and FIG. 12 illustrates a state in which a cartridge is withdrawn from a slot of an incubation chamber by the cartridge withdrawal driving unit 106 shown in FIG. 11. As shown in the drawings, the cartridge withdrawal driving unit 106 includes a motor 614, a belt 616, and an ejector 618.

When incubation in the cartridge located in a specific slot is completed, the control unit 114 drives the shelf elevation unit 804, so to locate the corresponding slot at the height of the chamber through-hole 612 or the chamber outlet 710. After that, the control unit 114 drives the ejector 618 by the motor 614 and the belt 616. The ejector 618 allows the cartridge 101 to be withdrawn from a specific slit of the incubation chamber 104 through the chamber outlet 710 and mounted in the cartridge holder 1201. An elastic body is installed at the front end of the ejector 618 to prevent the cartridge 101 from being excessively pushed into the cartridge holder 1201.

Figure 13:
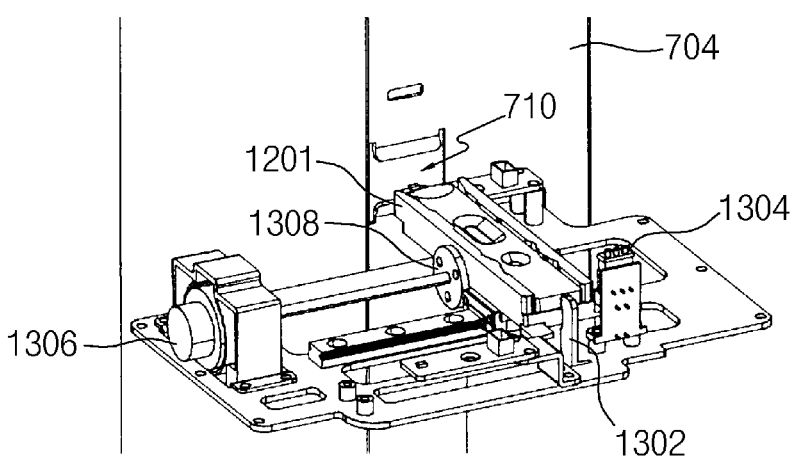
FIG. 13 illustrates the cartridge transfer driving unit shown in FIG. 3.

FIG. 13 illustrates the cartridge transfer driving unit shown 108 in FIG. 3. As shown in the drawing, the cartridge transfer driving unit 108 includes a cartridge holder 1201, a stopper 1302, a cartridge holder position sensor 1304, a motor 1306, and a moving block 1308.

When the cartridge 101 is mounted into the cartridge holder 1201 by the cartridge withdrawal driving unit 106, the stopper 1302 prevents the cartridge 101 from escaping from the cartridge holder 1201. The cartridge holder position sensor 1304 checks whether or not the cartridge holder 1201 is present at the position of the chamber outlet 710. The control unit 114 transfers the cartridge holder 1201 to the determination unit 110 by the motor 1306 and the moving block 1308.

Figure 14:
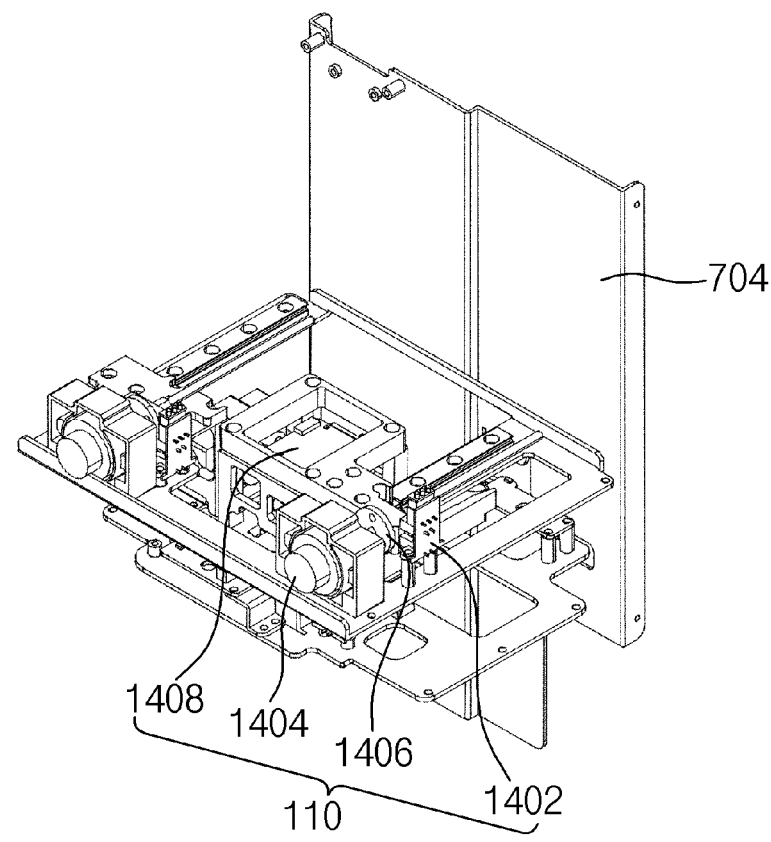
FIG. 14 illustrates the determination unit shown in FIG. 3.
Figure 15:
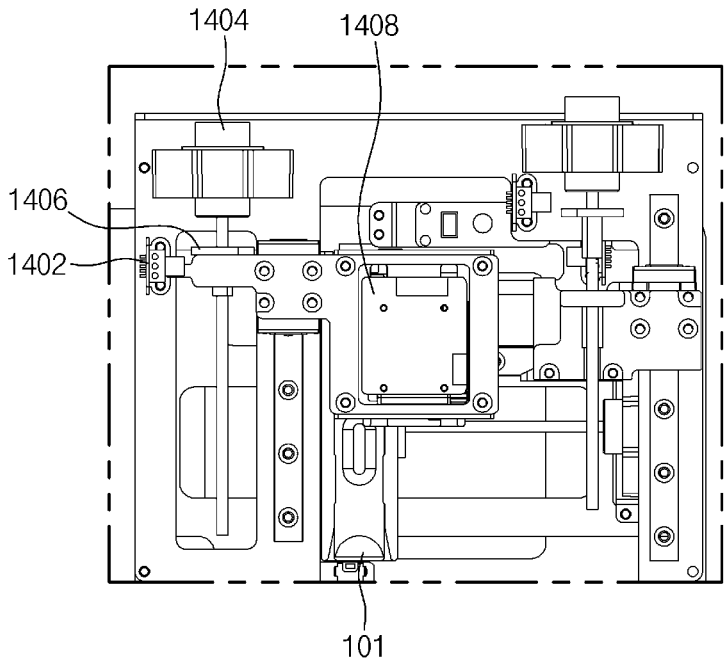
FIG. 15 illustrates a state in which the cartridge is transferred to the determining unit shown in FIG. 14.

FIG. 14 illustrates the determination unit 110 shown in FIG. 3, while FIG. 15 illustrates a state in which the cartridge 101 is transferred to the determining unit 110. As shown in the drawings, the determination unit 110 includes an initial position sensor 1402, a motor 1404, a moving block 1406, and an optical module 1408.

The control unit 114 drives the optical module 1408 by use of the motor 1404 and the moving block 1406. The moving block 1308 for transferring the cartridge moves in the width direction of the immune reaction analysis device 100, but the moving block 1406 for driving the optical module 1408 moves in the longitudinal direction of the immune reaction analysis device 100, so that the optical module 1408 can be accurately positioned in the cartridge 101. The control unit 114 accurately checks the initial position of the optical module 1408 by use of the initial position sensor 1402, and then drives the optical module 1408. The optical module 1408 scans the cartridge 101 with light to detect the reaction results from the cartridge 101, and sends the detection values to the control unit 114. The control unit 114 calculates a diagnosis result using the detection value transmitted from the optical module 1408, and outputs it by use of the user interface 15 or the built-in printer 16.

Figure 16:
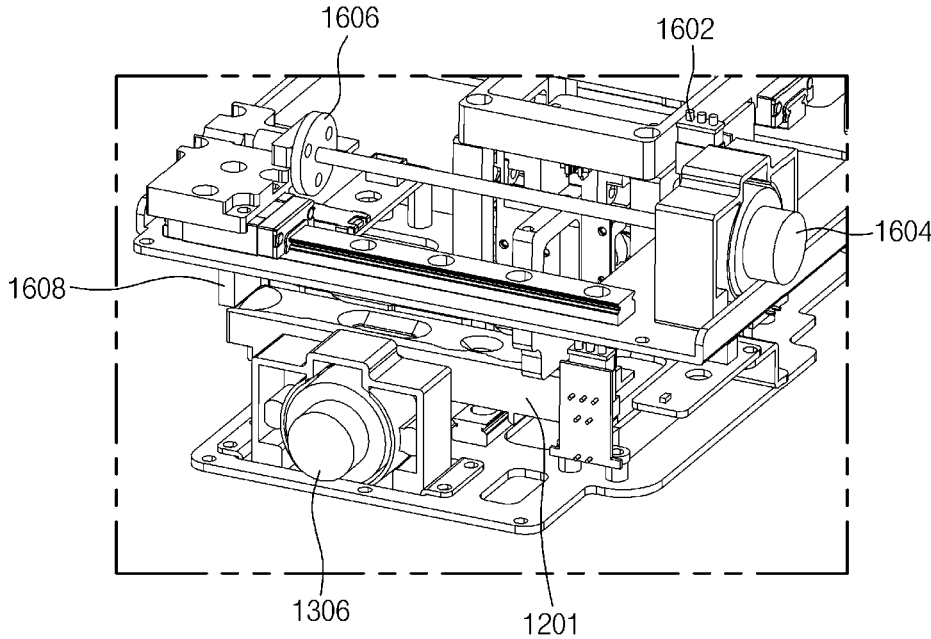
FIGS. 16 and 17 illustrate the cartridge discharge driving unit shown in FIG. 3.
Figure 17:
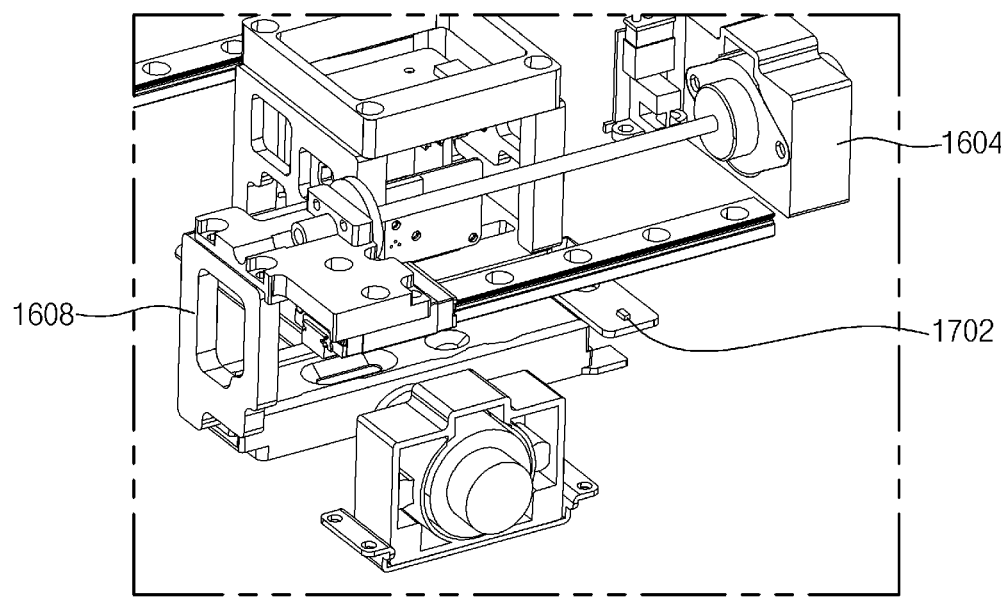
Figure 18:
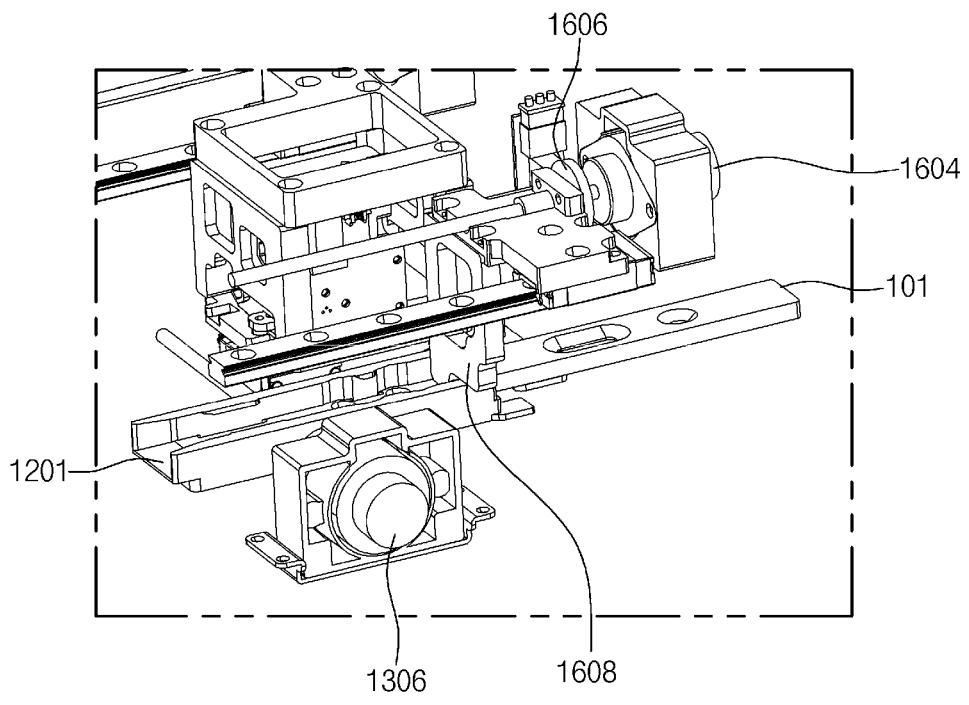
FIG. 18 illustrates a process of discharging a cartridge by the cartridge discharge driving unit shown in FIG. 16.

FIGS. 16 and 17 illustrate the cartridge discharge driving unit 112 shown in FIG. 3 while FIG. 18 illustrates a process of discharging a cartridge by the cartridge discharge driving unit 112. As shown in the drawings, the cartridge discharge driving unit 112 includes an initial position recognition sensor 1602, a motor 1604, a moving block 1606, a rake 1608, and a cartridge discharge sensor 1702.

After the optical module 1408 completes its detection, the cartridge 101 is transferred to the cartridge discharge driving unit 112 by the cartridge transfer driving unit 108. The control unit 104 checks the initial position of the cartridge discharge driving unit 112 by use of the initial position sensor 1602. The control unit 114 drives the rake 1608 by use of the motor 1604 and the moving block 1606 to pull the cartridge 101 mounted in the cartridge holder 1201. The cartridge 101 pulled by the rake 1608 is discharged to the outside through the cartridge outlet 17, and is automatically collected in a cartridge waste box (not shown) without user intervention.

If the cartridge holder 1201 is moved while the cartridge 101 has not been discharged yet and is hanging somewhere, there is a risk that the cartridge 101 may be damaged. Accordingly, the control unit 114 checks whether the cartridge 101 is completely discharged by means of the cartridge discharge sensor 1702, and then controls the cartridge discharge driving unit 112 so that the cartridge holder 1201 may be moved.

FIG. 19 illustrates one of the screens displayed on the user interface shown in FIG. 1A.

The barcode recognition module 512 recognizes the diagnosis type ("Item" in FIG. 19), lot number, and the like from the barcode of the cartridge 101. A lot is a unit of product produced at one time. The ID chip 19 contains formula information of the cartridge and the like. The control unit 114 converts the measurement result of the determination unit 110 into a diagnosis result ("Result" in FIG. 19) by using the formula information. The camera module 402 generates subject identification information ("Name" in FIG. 19). The subject identification information may be generated from the information written on the cartridge by handwriting. "Data&Time" indicates the time the diagnosis was made.

Although preferred embodiments of the present invention have been described in detail above, the scope of the present invention is not limited thereto, but various modifications and improvements made by those skilled in the art using the basic concept of the present invention as defined in the appended claims are also within the scope of the present invention.

The invention claimed is:

1. An immune reaction analysis device comprising:
an incubation chamber comprising a plurality of slits for accommodating cartridges, and in which an incubation for an immunodiagnostic reaction is performed;
a cartridge input driving unit configured for inputting the cartridge into the slit of the incubation chamber, and wherein the plurality of slits are disposed in the incubation chamber in a direction perpendicular to a driving direction of the cartridge input;
a determination unit configured for determining the result of the reaction in the cartridge;
a cartridge withdrawal driving unit configured for withdrawing the cartridge accommodated in the slit of the incubation chamber;
a cartridge transfer driving unit configured for transferring the withdrawn cartridge to the determination unit; and
a control unit configured for controlling the cartridge input driving unit, the cartridge withdrawal driving unit, and the cartridge transfer driving unit;
wherein the incubation chamber comprises a shelf, and the shelf is configured to form the plurality of slits, and wherein the plurality of slits are arranged in a vertical direction;
a shelf lifting unit configured for vertically driving the shelf, and a first cartridge sensor configured to be installed at an inlet of at least one of the plurality of slits;
and a second cartridge sensor is configured to be installed at an outlet of at least one of the plurality of slits.

2. The immune reaction analysis device of claim 1, further comprising:
a cartridge discharge driving unit for discharging a corresponding cartridge to the outside after determination of an immune reaction result inside the cartridge located in the determination unit is completely determined.

3. The immune reaction analysis device of claim 1, wherein the incubation chamber further includes a Peltier element attached to the shelf.

4. The immune reaction analysis device of claim 3, wherein the incubation chamber further includes a temperature sensor attached to the shelf;

wherein the control unit controls the Peltier element according to the measured value of the temperature sensor.

5. The immune reaction analysis device of claim 1, wherein the incubation chamber further includes a chamber case for accommodating the shelf and the shelf elevation unit.

6. The immune reaction analysis device of claim 5, wherein on the front surface of the chamber case, a chamber inlet for inputting a cartridge is formed at a first height and a chamber through-hole is formed at a second height.

7. The immune reaction analysis device of claim 6, wherein the cartridge input driving unit includes an injector for inputting a cartridge into a slit positioned at the first height of the incubation chamber through the chamber inlet.

8. The immune reaction analysis device of claim 6, wherein a chamber outlet is formed at the second height on the rear surface of the chamber case.

9. The immune reaction analysis device of claim 8, wherein the control unit drives the shelf elevation unit to position the slit from the first height to the second height after a preset incubation time elapses.

10. The immune reaction analysis device of claim 1, further comprising:

a camera module for photographing a housing of the cartridge which is input into a slit of the incubation chamber by means of the cartridge input driving unit; and a user interface for displaying a specific location of the cartridge housing photographed by the camera module.

11. The immune reaction analysis device of claim 1, further comprising:

a barcode recognition module for recognizing a barcode printed on the housing of the cartridge which is input into the slit of the incubation chamber by means of the cartridge input driving unit.

12. The immune reaction analysis device of claim 2, wherein the cartridge discharge driving unit includes a sensor for detecting whether or not the cartridge is discharged.

\* \* \* \* \*